United States Patent
Lesiv et al.

(10) Patent No.: US 12,115,232 B2
(45) Date of Patent: Oct. 15, 2024

(54) PREPARATION FOR MAGNETIC RESONANCE DIAGNOSTICS FOR ONCOLOGICAL DISEASES, COMPRISING DEUTERATED 3-O-METHYLGLUCOSE, AND DIAGNOSTIC METHOD USING SAID PREPARATION

(71) Applicant: SOLVEX LIMITED LIABILITY COMPANY, Moscow (RU)

(72) Inventors: Aleksei Valerievich Lesiv, Dolgoprudny (RU); Pavel Evgenievich Ivashkin, Moscow (RU); Mikhail Vladimirovich Gulyaev, Moscow (RU); Evgeniya Olegovna Dorofeeva, Moscow (RU); Aleksei Viktorovich Kosenkov, Moscow (RU); Mikhail Valentinovich Kiselevsky, Moscow (RU); Vladimir Ivanovich Polshakov, Moscow (RU)

(73) Assignee: SOLVEX LIMITED LIABILITY COMPANY, Moscow (RU)

( * ) Notice: Subject to any disclaimer, the term of this patent is extended or adjusted under 35 U.S.C. 154(b) by 0 days.

(21) Appl. No.: 16/765,934

(22) PCT Filed: Nov. 21, 2017

(86) PCT No.: PCT/RU2017/000869
§ 371 (c)(1),
(2) Date: May 21, 2020

(87) PCT Pub. No.: WO2019/103635
PCT Pub. Date: May 31, 2019

(65) Prior Publication Data
US 2020/0330618 A1     Oct. 22, 2020

(51) Int. Cl.
*A61K 49/10*  (2006.01)
*A61K 9/00*   (2006.01)
*C07H 3/02*   (2006.01)

(52) U.S. Cl.
CPC .............. *A61K 49/10* (2013.01); *C07H 3/02* (2013.01); *A61K 9/0053* (2013.01)

(58) Field of Classification Search
CPC ................................. A61K 49/10; A61K 9/00
See application file for complete search history.

(56) References Cited

U.S. PATENT DOCUMENTS

| 5,945,564 A | 8/1999 | Takayanagi | |
|---|---|---|---|
| 2002/0035071 A1* | 3/2002 | Pitha ................. | A61K 31/7004 514/23 |
| 2003/0211036 A1* | 11/2003 | Degani ................ | A61B 5/0263 702/19 |
| 2006/0172305 A1* | 8/2006 | Tidmarsh .............. | A61P 35/00 435/7.23 |
| 2007/0177143 A1* | 8/2007 | Chaiken ................ | G01N 21/65 600/475 |

FOREIGN PATENT DOCUMENTS

| CN | 106456807 | 2/2017 | |
|---|---|---|---|
| WO | 96/28190 | 9/1996 | |
| WO | 2005/063119 | 7/2005 | |
| WO | 2011/024156 A1 | 3/2011 | |
| WO | WO-2015145447 A2 * | 10/2015 | ............. A61K 49/10 |

OTHER PUBLICATIONS

Mackie W. et al. Nuclear magnetic resonance spectral observations on the glycol-scission of deuterated D-glucose. Canadian Journal of Chemistry. 2011, vol. 43, N. 10, pp. 2645-2651.
Michal Rivlin et al., "Functional molecular imaging of tumors by chemical exchange saturation transfer MRI of 3-O-Methyl-D-glucose", Magnetic Resonance in Medicine, vol. 72, No. 5, Nov. 2014, pp. 1375-1380.
W. Mackie et al., "Nuclear magnetic resonance spectral observations on the glycol-scission of deuterated D-glucose", Canadian Journal of Chemistry, Oct. 1965, vol. 43, No. 10, pp. 2645-2651.
Yuying Hwang et al., "Nonglycolytic Acidification of Murine Radiation-induced Fibrosarcoma 1 Tumor via 3-O-Methyl-D-glucose Monitored by $^1H$, $^2H$, $^{13}C$, and $^{31}P$ Nuclear Magnetic Resonance Spectroscopy", Cancer Research, Mar. 1, 1992, vol. 52, No. 5, pp. 1259-1266.

* cited by examiner

*Primary Examiner* — Michael G. Hartley
*Assistant Examiner* — Jagadishwar R Samala
(74) *Attorney, Agent, or Firm* — Nixon & Vanderhye PC (57) ABSTRACT

The invention relates to medicine, particularly to agents for magnetic resonance diagnostics for oncological diseases. Developed for this purpose are a diagnostic preparation and a diagnostic method based on using said diagnostic preparation, in which a deuterated derivative of 3-O-methylglucose or a mixture of at least two different deuterated derivatives of 3-O-methylglucose is used as said preparation. The method according to the invention includes conducting magnetic resonance imaging and/or magnetic resonance spectroscopy on deuterium nuclei at a time after administration of the diagnostic preparation sufficient for the diagnostic preparation to accumulate in the tumor tissue of a subject in order to produce a magnetic resonance image and/or a magnetic resonance spectrum accordingly. The proposed method enables a highly informed diagnosis of oncological diseases.

15 Claims, 10 Drawing Sheets

PREPARATION FOR MAGNETIC RESONANCE DIAGNOSTICS FOR ONCOLOGICAL DISEASES, COMPRISING DEUTERATED 3-O-METHYLGLUCOSE, AND DIAGNOSTIC METHOD USING SAID PREPARATION

This application is the U.S. National Phase of International Application No. PCT/RU2017/000869 filed on Nov. 21, 2017, the entire contents of which is hereby incorporated by reference herein.

TECHNICAL FIELD

The invention relates to medicine, in particular to the means for magnetic resonance imaging in oncology.

BACKGROUND

Diagnostics for cancer, including early-stage detection, is a priority for the global health care. One of the powerful diagnostic methods for such diseases is the magnetic resonance imaging (MRI).

Most varieties of the MRI applied in the clinical practice, are based on the detection of proton magnetic resonance signal ($^1H$ nuclei), which are part of the water molecules in the human body. $^1H$ MRI provides a high degree of anatomical detail and in many cases allows to detect areas with abnormal signal corresponding to the tumors. At the same time, from the clinical practice it is known that the MRI is not always capable to distinguish malignant tumors from benign ones, or those not requiring urgent treatment (low specificity of the method). In this context, early diagnosis of the oncological diseases is also hampered because of the high risk of a false positive result.

The main method of increasing the $^1H$ MRI diagnostic value is to use contrast agents that change the parameters of the signal in their vicinity [Topics in Current Chemistry, Contrast Agents I, Magnetic Resonance Imaging, Editors: Krause, Werner, 2002]. There is a wide range of contrast agents used in the MRI diagnostics, including commercially available Omniscan®, Magnevist®, ProHance®, and Clariscan®, which is a complex of gadolinium, as well as Feridex® and Resovist®, which are stable water suspensions of magnetic nanoparticles. These substances are injected into the bloodstream of the patient and assess the degree of blood supply to areas with suspected malignancy.

An alternative of performing $^1H$ MRI with contrast agents is a registration of the signal of the other nuclei, particularly $^{31}P$, $^{13}C$, $^{19}F$, $^2H$, $^{23}Na$. One of these nuclei is deuterium ($^2H$). This non-radioactive isotope of hydrogen, which natural content in biological objects is 0.0156%, and sensitivity is several times lower than that of the proton.

To date several cases of $^2H$ NMR and/or $^2H$ MRI application in vivo are described. The document US20030211036 A1 proposed a method of measuring the perfusion of the tumor tissues using isotope-labeled compounds, including deuterated compounds.

The document U.S. Pat. No. 5,042,488 demonstrated that it is possible to detect the background deuterium signal, as well as the signal resulting from the injection of $D_2O$ or 1-deuterated glucose in vivo (in a rat's liver). It is noted that the invention can also be implemented using other blood flow indicators labeled with deuterium.

The document US20100322865 A1 describes the use of metabolic precursors of water for estimating metabolic rate by carrying out the $^2H$-MRI. 1,2,3,4,5,6,6-deuterated glucose is given as an example of HOD metabolic precursor. Within the described invention only the deuterium NMR signals of the metabolic water and aliphatic chains of fatty acids are registered, but no NMR signals of the deuterated glucose.

Glucose consumption of the rat's brain based on the registered NMR spectra after the introduction of 6,6-deuterated glucose was assessed in vivo [Ming Lu et. al., Quantitative assessment of brain glucose metabolic rates in vivo using deuterium magnetic resonance spectroscopy, JCBFM, 2017, 1-13].

None of the above methods is used in practice for the diagnostics of the oncological diseases, to a large extent due to the need of using very large doses of the deuterated compounds.

Despite the prominence of existing modalities of MRI, there is a need to develop new, more efficient approaches for the MRI diagnosis of the oncological diseases.

SUMMARY OF THE INVENTION

The object of the present invention is the development of new efficient diagnostic agent for diagnosis of the oncological diseases through MRI and/or MR spectroscopy, and a diagnostic method comprising the use of the specified agent.

The invention concerns the discovery of a new and efficient diagnostic agent that can be used in the diagnostics of the oncological diseases, particularly breast cancer. Another technical result of the present invention is the development of the new efficient and informative diagnostic method for oncology by means of magnetic resonance imaging and/or magnetic resonance spectroscopy at the frequency of deuterium nuclei, that includes the administration of the diagnostic agent according to the invention, said agent being able to accumulate in tumors in a sufficient concentration to register a deuterium MR image or a $^2H$-NMR spectrum in vivo.

The diagnostic agent according to the invention is characterized by the combination of such properties as: high content of deuterium atoms; its ability to accumulate in tumors within a reasonable time up to a concentration that is sufficient for the diagnostics; low toxicity and and an almost complete excretion of the intact agent from the body. This allows for efficient diagnostics using dosages that are harmless to the human.

The method of the invention is not associated with any harmful effects of ionizing radiation (typical, for example, for the methods of CT, PET, SPECT), which in turn increases the safety of the studies and makes it possible to perform more frequent repeated studies, and makes the method suitable for pediatric patients. The invention is aimed at obtaining diagnostic information similar to that of the positron emission tomography (PET), but, unlike the latter, it allows to eliminate the risks associated with ionizing radiation of the radiopharmaceutical agents.

The present invention concerns the development of a diagnostic agent that includes a deuterated derivative of 3-O-methylglucose, or a mixture of at least two different deuterated derivatives of 3-O-methylglucose, for the diagnosis of oncological diseases by magnetic resonance imaging and/or magnetic resonance spectroscopy at the frequency of deuterium nuclei.

In particular embodiments of the invention, the diagnostic agent additionally includes at least one additional pharmaceutically acceptable component. In particular embodiments of the invention pharmaceutically acceptable component is a carrier, filler and/or solvent.

In particular embodiments of the invention the deuterated derivative of 3-O-methylglucose is 3-O-CD$_3$-glucose, 3-O-CD$_2$H-glucose, 3-O-CDH$_2$-glucose, 6,6-dideuterio-3-O-CD$_3$-glucose, 6,6-dideuterio-3-O-CD$_2$H-glucose, 6,6-dideuterio-3-O-CDH$_2$-glucose, 6,6-dideuterio-3-O—CH$_3$-glucose.

In the other particular embodiments of the invention, the diagnostic agent is a mixture of at least two different deuterated derivatives of 3-O-methylglucose, selected from 3-O-CD$_3$-glucose and/or 3-O-CD$_2$H-glucose and/or 3-O-CDH$_2$-glucose and/or 6,6-dideuterio-3-O-CD$_3$-glucose and/or 6,6-dideuterio-3-O-CD$_2$H-glucose and/or 6,6-dideuterio-3-O-CDH$_2$-glucose and/or 6,6-dideuterio-3-O—CH$_3$-glucose and/or any other deuterated derivatives of 3-O-methylglucose. In particular embodiments of the invention, the diagnostic agent optionally includes non-deuterated 3-O-methylglucose.

In particular embodiments of the invention components of the diagnostic agent contain atoms of deuterium that partially or completely substitute dissociable hydrogen atoms attached to the oxygen atoms besides the deuterium atoms associated with carbon atoms.

The invention also includes the process of obtaining the diagnostic agent according to the invention.

The present invention includes the implementation of the diagnostic method for oncological diseases, comprising the following stages:
  a) the diagnostic agent according to the invention is administered to the subject;
  6) after administration of the diagnostic medication, after a time sufficient for accumulation of the deuterated agent in the tumor, magnetic resonance imaging and/or magnetic resonance spectroscopy is carried out at the frequency of deuterium nuclei resulting in a $^2$H-MR image and/or a $^2$H-NMR spectrum, respectively;
  B) the presence or absence of an oncological disease is diagnosed based on the observed signal intensity of the deuterium nuclei, reflecting the level of accumulation of the diagnostic agent.

In particular embodiments of the invention, in the absence of accumulation areas of the diagnostic agent, a subject is diagnosed with absence of cancer.

In particular embodiments of the invention, at least one additional medical study is carried out, selected from the magnetic resonance imaging using nuclei differing from deuterium and/or ultrasound and/or computed tomography and/or x-ray and/or palpation and/or biopsy and/or analysis of biological fluids for tumor markers and/or radionuclide diagnostics and/or visual physical examination.

In particular embodiments of the invention the presence or absence of an oncological disease is diagnosed based on the comparison of signal intensity of deuterium nuclei with a typical intensity of the signal observed in healthy subjects in the corresponding tissue or organ.

In particular embodiments of the invention the presence or absence of an oncological disease is diagnosed based on the comparison of a signal intensity of the deuterium nuclei in the regions corresponding to normal and abnormal tissue according to additional medical studies.

In particular embodiments of the invention the presence or absence of an oncological disease is diagnosed based on a comparison of deuterium MR image with the image obtained through $^1$H-MRI.

In particular embodiments of the invention the presence or absence of an oncological disease is diagnosed based on the comparison of a signal intensity of the deuterium nuclei in the neighboring voxels that are located at different sides of the interface between the normal tissue and tissue suspicious for a tumor according to $^1$H MRI.

In particular embodiments of the invention based on the observed signal intensity of the deuterium nuclei, the conclusion about the malignancy or aggressiveness or degree of differentiation of the tumor is made.

In particular embodiments of the invention, the diagnosed oncological disease is a breast cancer.

In particular embodiments of the invention, the selective excitation of deuterium nuclei of the diagnostic agent is used during the registration of the MR image.

In particular embodiments of the invention, during the registration of the MR image the broadband excitation of the deuterium nuclei of the diagnostic agent is used.

In particular embodiments of the invention, the diagnostic agent is administered to a subject orally.

In the other particular embodiments of the invention, the diagnostic agent is administered to a subject parenterally.

In particular embodiments of the invention the magnetic resonance imaging and/or magnetic resonance spectroscopy on the deuterium nuclei is carried out 20-210 minutes after the administration of the diagnostic agent.

In particular embodiments of the invention, the diagnostic agent is administered to a subject in an amount corresponding to 1-3.5 g of deuterated derivative of 3-O-methylglucose or mixture of deuterated derivatives of 3-O-methylglucose per 1 kg of body weight of a subject.

The invention also includes the use of the diagnostic agent according to the invention for diagnostics of an oncological disease by the magnetic resonance imaging and/or magnetic resonance spectroscopy at the deuterium frequency.

DEFINITIONS AND TERMS

For a better understanding of the present invention below are some terms used in this description of the invention.

In the description of this invention, the terms "includes" and "including" are interpreted as meaning "includes, among other things". These terms are not meant to be interpreted as "consists only of".

The term deuterated or "deuterated derivative" in this document refers to a compound containing deuterium associated with carbon in excess of its natural content, at least in one position. In particular embodiments of the invention, the deuterium content, at least in one position, exceeds 30%, in other particular embodiments—90%. The symbol "D" in this document denotes a hydrogen atom that is enriched with $^2$H isotope with respect to its natural content. The "mixture of at least two different deuterated derivatives" refers to a mixture of compounds containing deuterium in different positions of the molecule, or containing different amounts of deuterium in the same position.

The term "voxel" in this document refers to a volume element in the sample that is freely selectable by adjusting the parameters of the magnetic field and produces the signal of the nuclear magnetic resonance.

The diagnostic agent according to the invention may include one or more pharmaceutically acceptable excipients that are suitable for specific forms of dosing, in particular, any carriers, solvents and/or excipients, which may be introduced into a patient's body together with the compound constituting the essence of this invention, and which do not negatively impact the deuterated compound, and are non-toxic when administered.

DETAILED DESCRIPTION OF THE INVENTION

The accumulation of very small amounts of radioactively labeled [$^{18}$F] fluorodeoxyglucose in tumors is a well-studied phenomenon and is used for diagnostics in positron emission tomography (PET). However, a relatively low sensitivity of MRI and the background content of deuterium in water (HOD) and tissues require a much higher concentration of the deuterium-based diagnostic agent in tumor compared to PET. Thus, [$^{18}$F] fluorodeoxyglucose is used in dosages on the order of $10^{-11}$ mol/kg (considering a typical specific activity of about $10^3$ Ci/mol and a typical dose about 10 mCi), but such data do not allow to predict the efficiency of accumulation of the deuterated compounds in tumor cells up to a level required to implement the present invention (as a result of the authors research, practically applicable doses of the agent of the present invention are on the order of $10^{-3}$ mol/kg).

For the successful implementation of a diagnostic method for oncological diseases using $^2$H MRI or $^2$H NMR one needs to achieve a sufficiently high deuterium concentration in the tumor tissue. To satisfy this criterion, a diagnostic agent:
 1) should quickly and selectively accumulate in the tumor tissue (in particular, there should be a sufficiently efficient mechanism of membrane transport);
 2) should be characterized with a rather slow excretion (which allows sufficient time for the accumulation of large quantities of the agent in the tumor, as well as for an extended registration of $^2$H MR images);
 3) should not be significantly metabolized (minimizing possible side effects, including the incorporation of deuterium into the biomolecules, and allowing a repeated examination in as little as a few hours after the previous administration, without changing the background signal of the tumor);
 4) should have low toxicity at the concentrations required (making it possible to administer sufficiently large doses of the agent);
 5) should contain a large amount of deuterium (required to achieve sufficient signal intensity).

The authors of this invention have studied various derivatives of glucose as a potential diagnostic agent. It was discovered that not all glucose derivatives can be used for the diagnostics of oncological diseases through $^2$H MRI or $^2$H NMR. Thus, in particular, preliminary experiments with 6,6-D$_2$-glucose indicate that it is not possible to accurately visualize the tumor when using this compound (due to weak contrast, low signal/noise rate).

Unexpectedly it was discovered that deuterated derivatives of 3-O-methylglucose are capable of accumulating in tumor tissue in sufficient concentration to visualize tumors in vivo by $^2$H MRI method or $^2$H NMR, which in turn enables an efficient diagnosis of oncological diseases by the magnetic resonance imaging on the deuterium nuclei.

Due to the low content of deuterium in the body (0.015% of hydrogen atoms), background signals in the $^2$H MRI are several orders of magnitude lower than in $^1$H MRI. The development of similar methods using non-deuterated diagnostic agents on the basis of $^1$H MRI is complicated because of the presence of a large number of background signals of natural low molecular weight compounds with intensity comparable to the maximum achievable signal intensity of non-deuterated diagnostic agents. At the same time, the presence of the background HOD signal imposes restrictions on the minimum acceptable concentration for $^2$H MRI of a diagnostic agent in the tumor. The practical applicability of the diagnostic method according to the invention depends on its pharmacokinetics and pharmacodynamics.

The ability to register the deuterium signal in vivo is also determined by the presence of a sufficient number of deuterium atoms in the structure of the compound. So the diagnostic agent according to the invention, comprising deuterated 3-O-methylglucose containing CD$_3$ group and/or CD$_2$OH group, is the preferred embodiment of the present invention. The presence of such deuterated groups allows to carry out MRI scans with the use of lower concentrations of the diagnostic agent, which minimizes side effects.

The method of the invention allows to diagnose the presence or absence of an oncological disease. The method according to the invention is based on the use of a deuterated diagnostic agent and the registration of MRI and/or NMR spectra at the frequency of deuterium.

It is known that $^1$H MRI by itself in many cases has insufficient diagnostic accuracy, whereas the method of the invention provides information about the molecular transportation of glucose, not available in traditional modes of $^1$H MRI, and thus potentially allows to obtain more accurate diagnostic information.

In one of the embodiments of the invention, the process of diagnostics involves MRI and is carried out as follows:

a) in some embodiments of the invention $^1$H MRI is carried out. Registration of $^1$H MRI allows, first, establish an anatomical reference frame for the deuterium signal, and secondly, to identify areas with suspected malignancy (in other embodiments of the invention, the definition of the field of view of $^2$H MRI can be carried out in other ways, in particular by ultrasound, computed tomography, radiography, palpation, biopsy, analysis of biological fluids for tumor markers, radionuclide diagnostics, physical examination);

b) the diagnostic agent is administered;

c) after a time sufficient for accumulation of the diagnostic agent in the tumor tissue of a subject the $^2$H MR image is registered at the frequency of precession of the deuterium nuclei of the diagnostic agent;

d) obtained deuterium MR images are analyzed to find areas with anomalously high intensity and, therefore, responsible for the accumulation of the diagnostic agent. In particular, it is possible to compare the images obtained at $^1$H and $^2$H: if abnormal areas on $^1$H and $^2$H are matching, this means a higher probability of the present malignancy. However, the presence of abnormalities on $^1$H MR image is not a prerequisite: there may be situations when the tumor is not seen on the image obtained through $^1$H MRI, while the accumulation of the diagnostic medication is observed on the image obtained by $^2$H MRI. In the latter case, $^1$H MRI is used only for anatomical binding of a suspicious area.

In another particular embodiment of the invention, the process of diagnosis involves performing NMR spectroscopy at the frequency of deuterium and is carried out as follows:

a) $^1$H MRI is performed to identify regions with suspected malignancy (in other embodiments of the invention, the definition of the field of $^2$H NMR can be carried out in other ways, in particular by ultrasound, computed tomography, radiography, palpation, biopsy, analysis of biological fluids for tumor markers, radionuclide diagnostics, physical examination);

b) the diagnostic agent is administered;

c) after a time sufficient for accumulation of the diagnostic agent in the tumor tissue of a subject the spectrum of deuterium is registered (in particular, using local spectroscopy) in the voxels corresponding to the region of suspected malignancy (e.g., according to the results of $^1$H MRI); optionally the spectrum is registered in neighboring voxels or the signal intensity is compared; in particular embodiments the spectroscopy can be performed using transmitting, transmitting-and-receiving, volume, implanted, or surface coils;

d) the signal intensity in voxels corresponding to the region of suspected malignancy is compared to: (i) typical values for this tissue (which shall be first defined in healthy subjects) and/or (ii) the intensity of the neighboring voxels corresponding to the same tissue or organ, and free of anomalies according to $^1$H MRI. Increased signal intensity suggests the accumulation of the diagnostic agent and, as a consequence the presence of a malignancy.

The order of the stages a), b), c) in both of the above specified embodiments of the invention may be different, for example, the diagnostic agent is administered, $^1$H MRI is carried out, then $^2$H MRI or NMR spectroscopy is performed; or $^1$H MRI is done after $^2$H MRI or $^2$H NMR spectroscopy.

In particular embodiments of the invention, after identifying the region with suspected malignancy individual voxels lying within and outside the suspicious region are selected (in particular, a series of the neighboring voxels lying on the same line crossing the border of a suspicious area can be selected). Registration of the integral signal of $^2$H or $^2$H spectra in the selected voxels with the following comparison of their intensity in the $^2$H channel allows quickly and with greater sensitivity to detect the accumulation of the diagnostic agent.

MR images and MR spectra according to the invention can be acquired using any MRI machine equipped to register the signal of deuterium.

In particular embodiments of the invention, the use of the diagnostic agent, giving a signal in the region free of the background HOD signal, allows to carry out MRI with the use of selective excitation impulse configured on the frequency of the diagnostic agent. This eliminates the background signal of HOD on the image.

Through the use of molecular mechanisms of transportation and accumulation of the diagnostic agent according to the invention in cells, the method according to the invention enables the assessment of the metabolic activity of the tissue studied, and, consequently, to assess the malignancy or aggressiveness of the tumor. Thus the diagnostic potential of the method is increased compared with the conventional $^1$H magnetic resonance imaging and the MRI methods based on the evaluation of perfusion (including typical contrast agents).

The signal of the diagnostic agent according to the invention may be registered up to 3 hours after administration, and distribution of the agent in the tumor and other organs changes during this time. Thus, the signal of the diagnostic agent is primarily manifested in the kidneys, then in some areas of the tumor, probably corresponding to the areas of the most active growth and with the best blood supply. The maximum signal of deuterium in the whole volume of the tumor after intraperitoneal injection is observed in about 1 hour, then the pattern of the diagnostic agent distribution keeps on changing, and the tumor areas with the best blood supply are first to lose the diagnostic agent. Because of such behavior, repeated imaging over several hours after administration of the diagnostic agent according to the invention allows to obtain information on the speed of its accumulation and escape for individual parts of the tumor and to estimate the total volume of the tumor. Obtaining such an information about the structure of the tumor, and its typical dynamics of accumulation, using, for example, short-lived $^{11}$C-labeled analog for PET is not possible due to its very short half-life (20 minutes) and the impossibility of increasing the dose of the radiopharmaceutical due to a concomitant increase in the radiation load.

The experiments by the authors demonstrate the selectivity of accumulation of the agent according to the invention in tumor tissue compared to liver, skeletal muscles and other organs and tissues in acceptable to $^2$H MRI doses. It was also found that upon the introduction of equivalent doses of the diagnostic agent according to the invention to animals with various tumors there are differences in the dynamics of accumulation and the maximum intensity for deuterium correlated with a tumor type. In combination with $^1$H MRI data or other additional diagnostic methods, the agent and the method of the invention can be used to identify tumors in cases where its type is unknown.

The research conducted by the authors demonstrated good tolerability of the diagnostic agent by animals, the absence of apparent side effects when used in indicated doses and complete removal of the deuterium-containing compounds from the body within a few hours. So, after intraperitoneal injection of the agents according to the invention to mice at a dosage of 8 g/kg no lethality in the animals was observed. 6 hours after the administration the agent was not observed in the tumor according to the $^2$H magnetic resonance imaging. The background concentration of deuterium in the tumor and other tissues remained unchanged. Since the use of the diagnostic agent according to the invention is not associated with inclusion of the deuterated compounds in metabolic processes, the likelihood of long-term side effects is decreased. In addition, complete removal of deuterium from tumor tissue allows for repeated diagnostics, for example, after 6 hours and to monitor the dynamics of tumor development in the course of treatment.

The experiments showed that the results of the visualization of the tumor are significantly dependent on the dose of the diagnostic agent within the allowed range. Smaller doses allow to selectively visualize parts of the tumor with the most intense absorption, while increasing the dose leads to more complete filling of the boundaries of the tumor with the signal of deuterium. Because of this property of the diagnostic agent according to the invention it is possible to conduct dynamic studies (multiple registration of the images) with a gradual increase in concentration of the agent in blood with time (e.g., slow intravenous infusion or series of successive injections of small doses of the agent). Such studies can provide information on metabolic activity of different parts of the tumor and on the extent of an oncological disease.

The diagnostic method according to the invention can be applied, in particular, for early diagnostics of tumors of different localization, metastatic lesions, evaluating tumor response to treatment and conclusions about the efficiency of the therapy, to confirm the diagnosis made on the basis of the $^1$H MRI results and/or other diagnostic methods.

The method of the invention extends the existing methods of oncological diagnostics and enables an efficient diagnostic modality.

The Implementation of the Invention.

The possibility of objective manifestations of the technical result when using the invention is confirmed by reliable data given in the examples, containing experimental information obtained in the process of conducting research on methods adopted in this area. The invention is illustrated by the figures.

It should be understood that these and all examples given in the application materials are not limiting and are provided only to illustrate the present invention.

The examples given in this document illustrate the principle of the developed method, and do not limit the range of used doses and time interval between introduction of the diagnostic agent and detection of deuterium, because, depending on the sensitivity and other parameters of the equipment used, diagnosed disease and the nature of a subject (human or laboratory animal) the required dose and time required for accumulation may differ. Furthermore, parameters of registration of the spectra and images, including the time of signal accumulation, are part of the specific embodiments of the invention and can vary depending on the equipment used and the specific diagnostic task.

Synthesis of 3-O-CD$_3$-Glucose

D-glucose diacetonide (5 g, 19.2 mmol) is dissolved in DMF (10 ml), while cooling to 0° C. and stirring NaH (60%) (1.1 g) is added. The reaction mixture is kept under stirring for 1 hour at the room temperature, and then CD$_3$I (1.5 ml) is added dropwise. After 2 hours the reaction mixture is poured into ice water and the organic phase is extracted with ethyl acetate, twice washed with water. The organic phase is evaporated, then dissolved in THF (15 ml); CF$_3$COOH (2 ml) and water (1 ml) are added. The reaction mixture is boiled for 5 hours. Then 10 ml of toluene are added and evaporated. 3-O-CD$_3$-glucose (2.6 g, 70%) is extracted of the column chromatography residue on silica gel.

α-Isomer: $^1$H NMR (600 MHz, D$_2$O): δ 5.21 (d, 1H, $J_{1-2}$=3.7 Hz, H-1), 3.83 (m, 2H, H-4, H-6$^A$), 3.74 (dd, 1H, $J_{5-6B}$=5.4 Hz, $J_{6A-6B}$=12.4 Hz, H-6$^B$), 3.58 (m, 1H, H-2), 3.47 (m, 2H, H-3, H-5). $^{13}$C NMR (151 MHz, D$_2$O): δ 93.3 (C-1), 83.8 (C-3), 72.7 (C-4), 72.2 (C-2), 70.3 (C-5), 61.7 (C-6). β-Isomer: $^1$H NMR (600 MHz, D$_2$O): δ 4.84 (d, 1H, $J_{1-2}$=7.3 Hz, H-1), 3.88 (dd, 1H, $J_{5-6A}$=1.8 Hz, $J_{6A-6B}$=12.4 Hz, H-6$^A$), 3.70 (dd, 1H, $J_{5-6B}$=5.4 Hz, $J_{6A-6B}$=12.4 Hz, H-6$^B$), 3.47 (m, 2H, H-4, H-5), 3.28 (m, 2H, H-2, H-3). $^{13}$C NMR (151 MHz, D$_2$O): δ 97.1 (C-1), 86.5 (C-3), 77.0 (C-4), 74.7 (C-2), 70.2 (C-5), 61.9 (C-6).

Similarly, when using the reagent of the general formula CH$_x$D$_{(3-x)}$I (0<x<3) partially deuterated 3-O—(CH$_x$D$_{(3-x)}$)-glucose is obtained. When 6,6-dideuterio-D-glucose diacetonide is used as a substrate in combination with the reagent of CH$_y$D$_{(3-y)}$I (0≤y≤3) type 3-O—(CH$_y$D$_{(3-y)}$-6,6-dideuteroglucose (in particular, 3-O-methyl-6-deuterated glucose or 3-O-CD$_3$-6,6-dideuteroglucose) is obtained.

When using CF$_3$COOD and/or D$_2$O in the removal of protective groups and also by keeping the end product in D$_2$O followed by evaporation a deuterated 3-O-methylglucose with partially or fully deuterated hydroxyl groups is obtained.

Figure 1:
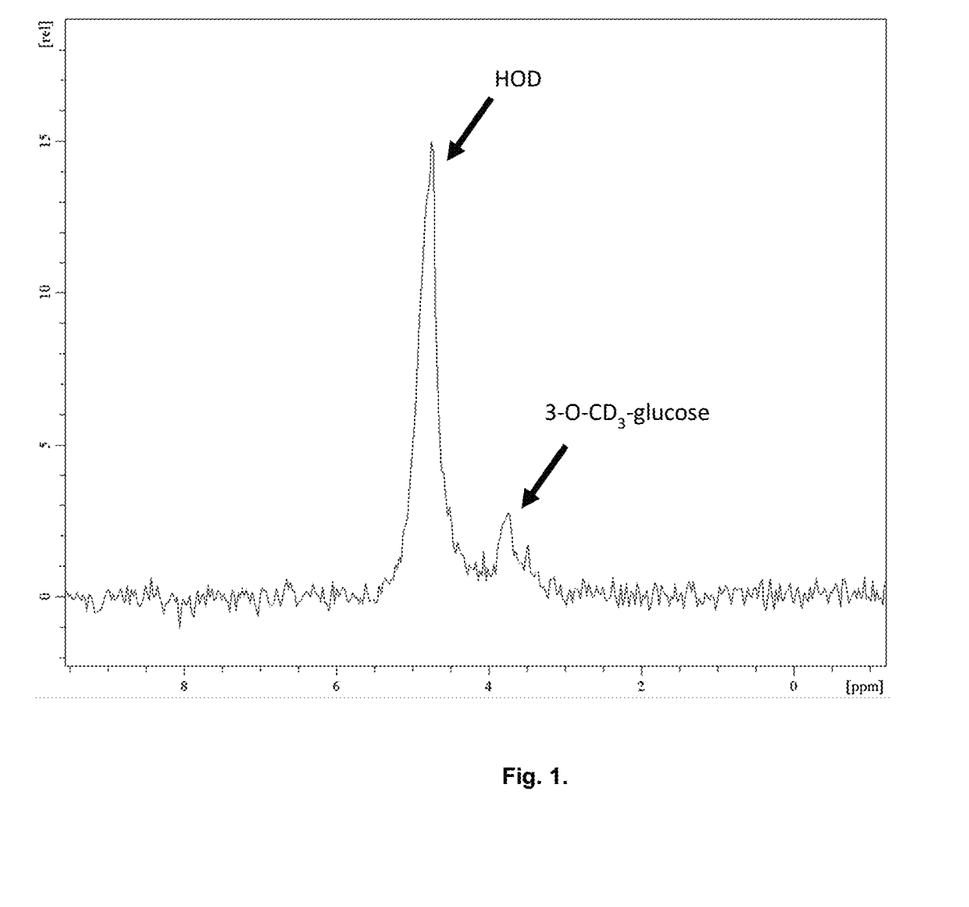
FIG. 1. $^2$H NMR spectrum of the phantom modeling the accumulation of 3-OCD$_3$-glucose in the tumor in the body of an animal.

To demonstrate the possibility of the NMR deuterium signal registration when accumulated in a limited volume of small amounts of the diagnostic agent, an experiment was conducted with a phantom that simulates the accumulation of 3-OCD$_3$-glucose in the tumor in the body of an animal (example 1, FIG. 1). It is shown that the method sensitivity is sufficient for registration of small quantities of 3-OCD$_3$-glucose (5 mmol distributed in a volume of 1 ml) using deuterium imaging.

It is possible to register a deuterium MR image of the sample containing a solution of 3-OCD$_3$-glucose with the use of the broadband and selective radio-frequency impulse (example 2).

Experiments in vivo (example 3, 4) demonstrate the possibility of deuterium imaging and NMR in vivo and the ability of 3-OCD$_3$-glucose to accumulate in tumors. The possibility of tumors diagnostics is demonstrated, in particular, for breast tumors, based on the observed signal of the deuterated diagnostic agent.

In the examples below, the MRI scanner Bruker BioSpec BC70/30 USR with the constant field of 7.05 T, equipped with a surface transmitting-and-receiving coil with a diameter of 3 cm and a scan depth of ca. 1 cm was used.

To register deuterium image the FLASH (Fast low angle shot) pulse sequence was used.

For experiments with the broadband excitation the following settings were used: the excitation frequency was determined by $^2$H NMR spectrum and was sfo1≈46.1745 MHz, a rectangular excitation pulse with a width of 1300 Hz and a power of 36 dB, the flip angle FA=30°, the repetition time TR=11.8 MS, echo time TE=4.4 msec, a scan area of 10 cm×10 cm, scan matrix, 50×50, slice thickness 3 cm, bandwidth of 12500 Hz, total scan time 10 minutes (1030 averages).

For experiments with selective excitation the following settings were used: excitation frequency sfo1=46.1745 MHz, a rectangular excitation pulse with a width of 130 Hz and a power of 48 dB, the flip angle FA=30°, the repetition time TR=25 MS, echo time TE=10 MS, a scanning area of 10 cm×10 cm, scan matrix 50×50, slice thickness 3 cm, bandwidth of 25,000 Hz, total scan time 10 minutes.

Example 1. Registration of $^2$H Spectrum of the Diagnostic Agent Concentrated in a Small Volume of the Phantom (the Model of Accumulation of 3-OCD$_3$-Glucose in the Tumor in the Body of an Animal)

To demonstrate the possibility of registration of the deuterium signal of small quantities of 3-OCD$_3$-glucose in a limited volume the following experiment was carried out.

A solution of 1 mg (5 umol) of 3-OCD$_3$-glucose in 1 ml of distilled water (with a natural content of deuterium) was placed in a cylindrical plastic vial with a volume of 1.5 mL. The resulting vial with the solution was placed in a cylindrical plastic container with a volume of 50 ml and 25 mm in diameter, filled with distilled water (with a natural content of deuterium). The obtained system of containers was located in the cavity of the scanner. The surface transmitting-and-receiving coil with a diameter of 3 cm and a scan depth of about 1 cm was located directly above the inner vial. Spectrum of deuterium was removed from the reference frequency 46.1746780 MHz. The pulse sequence consisting of one 90° pulse (256 averages, the delay between pulses is 0.1 s) was applied.

The FIG. 1 shows the spectrum of deuterium obtained in the above experiment. The large peak corresponds to HOD signal (the natural content of 15 mmol/l), the small peak corresponds to deuterated 3-O-methylglucose. This experiment demonstrates that $^2$H NMR spectroscopy using the surface coil has a sensitivity sufficient to register such small amounts of 3-O-methylglucose as 5 mol volume of 1 ml, surrounded by a large excess of water.

Example 2. The Registration of the Deuterium MR Image of the Sample Containing a Dilute Solution of Deuterated Diagnostic Agent To demonstrate the possibility to register deuterium tomogram of the diagnostic agent in dilute solution the following experiment was carried out.

The glass vial containing 5 ml solution of 3-O-CD$_3$-glucose (20 mg) in distilled water is placed in the cavity of the scanner. The surface transmitting-and-receiving coil with a diameter of 3 cm and a scan depth of about 1 cm was located directly above the vial.

Figure 2:
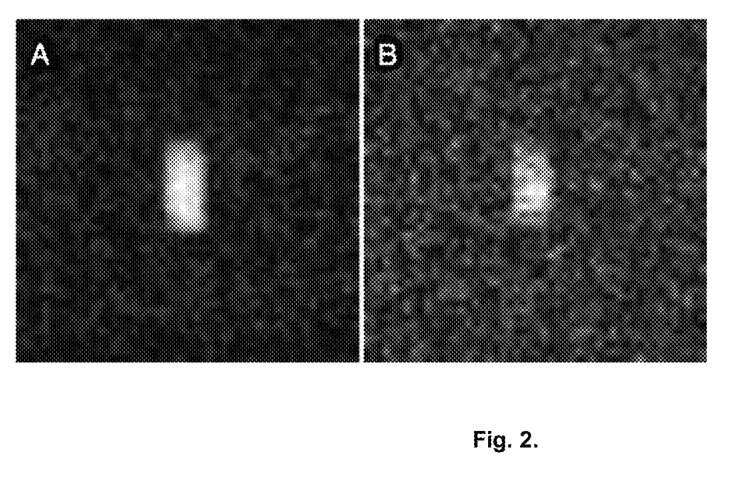
FIG. 2. Deuterium MRI of the phantom containing a dilute solution of deuterated diagnostic agent obtained using (a) broadband excitation, b) selective excitation at the frequency of 3-O-methylglucose.

FIG. 2 shows the deuterium images of the sample with a 3-O-CD$_3$-glucose obtained with the use of the broadband (left) and selective (right) excitation.

Example 3. The Accumulation of 3-OCD$_3$-Glucose in the Tumor of the Mouse

In this experiment, the following was used: an outbred mouse with a spontaneous tumor in the abdominal region and an outbred control mouse without tumor.

The animal with the weight of 30 g was injected intraperitoneally with a solution of 60 mg 3-O-CD$_3$-glucose in 0.3 ml of saline. After injection, the animal was kept in a separate cage with free access to food and water for 70 min. For shooting spectra the animal was immobilized with "isoflurane" agent. The surface transmitting-and-receiving coil was fixed on the body of the mouse successively in four positions (head, chest, pelvis, close to the tumor). Deuterium spectra were recorded on the Bruker BioSpec MRI tomograph BC70/30 USR, with constant field of 7.05 T with a reference frequency 46.1746780 MHz. The sequence consisting of one 90° pulse (64 accumulations, delay between pulses of 2 s) was used.

Figure 3:
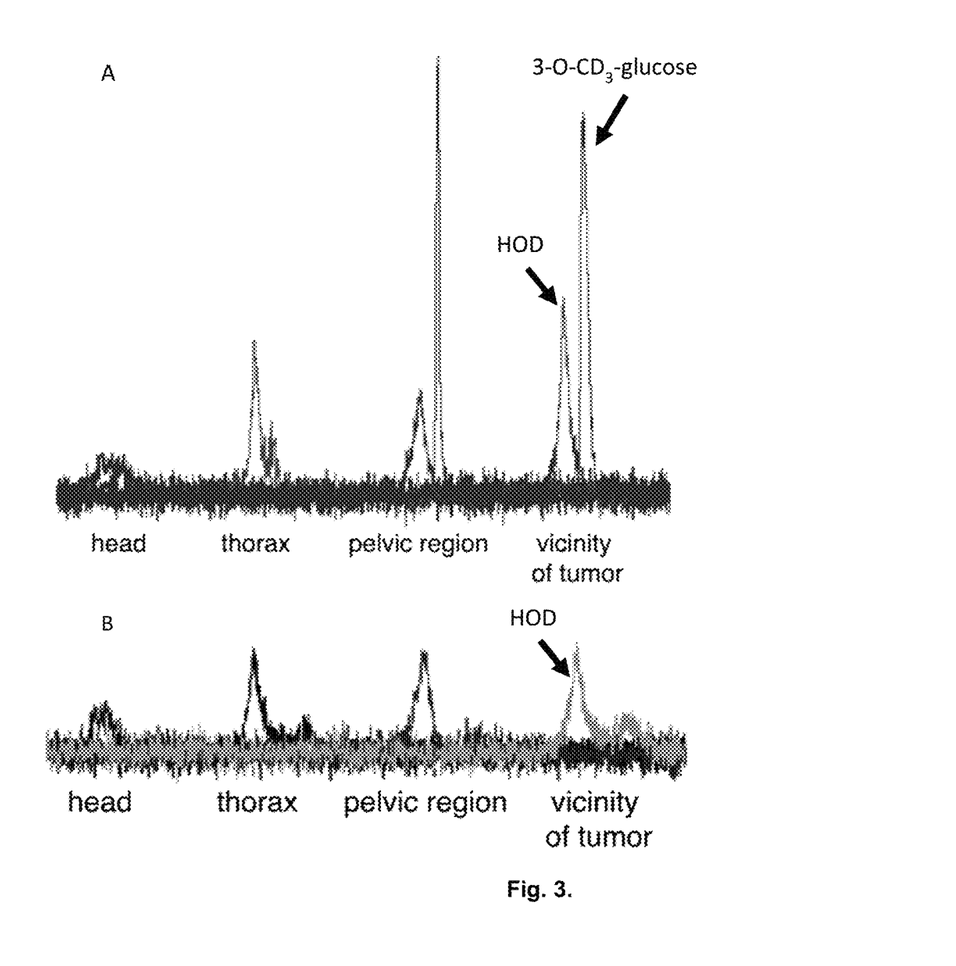
FIG. 3. The distribution of 3-OCD$_3$-glucose in the body of a mouse with a tumor in the abdominal region (a) and control mouse without tumor (b) 70 minutes after agent administration.

FIG. 3 shows the distribution of deuterated 3-methylglucose in the body of a mouse with tumor (FIG. 3, a) and control mouse without tumor (FIG. 3, b) in 70 minutes after agent administration (from left to right: head, chest, pelvis, close to the tumor). As it can be seen in the figure, in the case of the mouse with no tumor 3-OCD$_3$-glucose is completely eliminated, while the mouse with the tumor retains the deuterium signal in the area of the tumor which indicates the presence of the neoplastic disease. The experiment shows the possibility of accumulation of 3-O-CD$_3$-glucose in the tumor in sufficient concentration to be detected with deuterium spectroscopy.

Example 4. The Use of Deuterium MRI for Imaging Breast Carcinoma of the Mouse 4T1 In Vivo Using 3-OCD$_3$-Glucose as the Diagnostic Agent In this example, experiments were conducted on mice Balb/c inoculated with breast carcinoma 4T1 (injection of $5\times10^5$ cells/60 μl under the left front paw for 10 days before experiment) and in healthy Balb/c mice.

A solution of 20-72 mg of 3-O-CD$_3$-glucose was administered to an animal weighing 20 g was injected intraperitoneally, intravenously or via gavage (intraperitoneal: 0.5 ml of a saline solution; intravenous: 0.2 ml of water; oral: 0.25 ml of a saline solution). After injection, the animal was kept in a separate cage with free access to food and water within specified time. For imaging the animal was immobilized with isoflurane. The surface transmitting-and-receiving coil was fixed on the body of the mouse from the dorsal side in the thoracic region. The FIGS. 4-10 show $^2$H tomograms obtained with the use of the broadband excitation of the deuterium nuclei.

Figure 4:
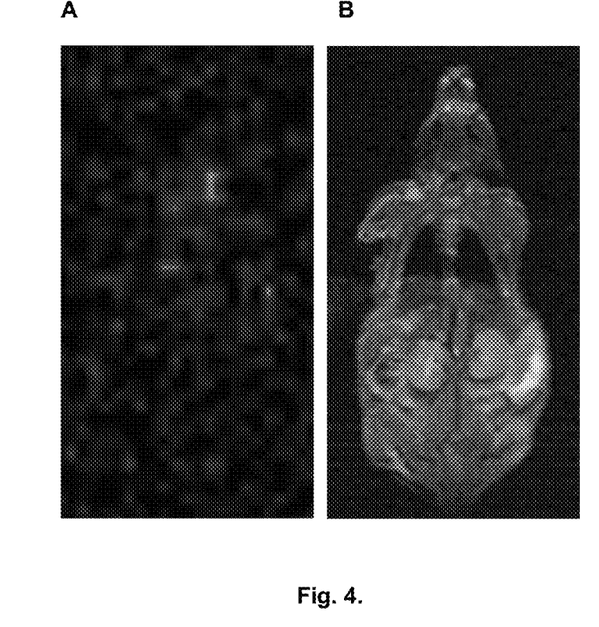
FIG. 4. MRI of a control mouse without tumors 40 min after the administration of 72 mg of 3-OCD$_3$-glucose:
  a) $^2$H MR image;
  b) $^1$H MR image.

FIG. 4 shows the image obtained for a control mouse no. 1 without tumors 40 minutes after intraperitoneal administration of 3-O-CD$_3$-glucose (a) $^2$H MRI; b) $^1$H MRI). This figure is missing an area with a strong signal of deuterium.

Figure 5:
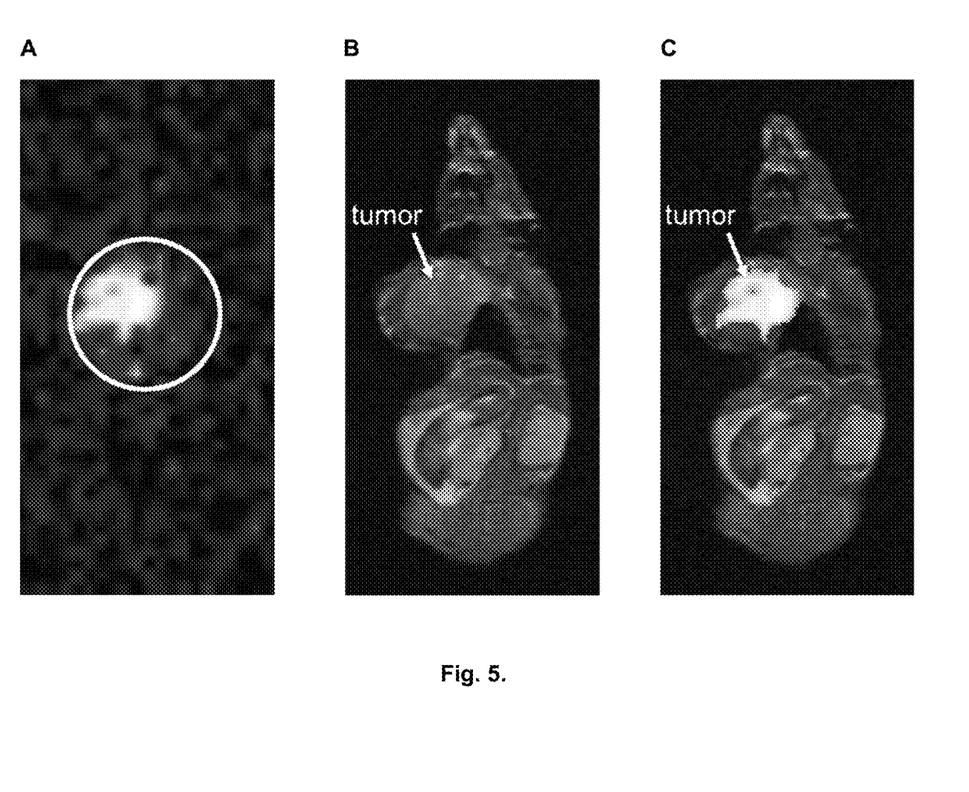
FIG. 5. MRI of a mouse with the breast carcinoma 4T1 20 min after the administration of 72 mg of 3-OCD$_3$-glucose:
  a) $^2$H MR image (the position of the surface coil is shown with a white dashed circle);
  b) $^1$H MR image;
  c) the combined image.

FIG. 5 shows the image obtained for the mouse no. 2 with the tumor 20 min after intraperitoneal injection of 3-O-CD$_3$-glucose: (a) $^2$H MRI (the position of the surface coil is shown in white contour); b) $^1$H MRI; C) the superposition of $^2$H MRI and $^1$H MRI).

Figure 6:
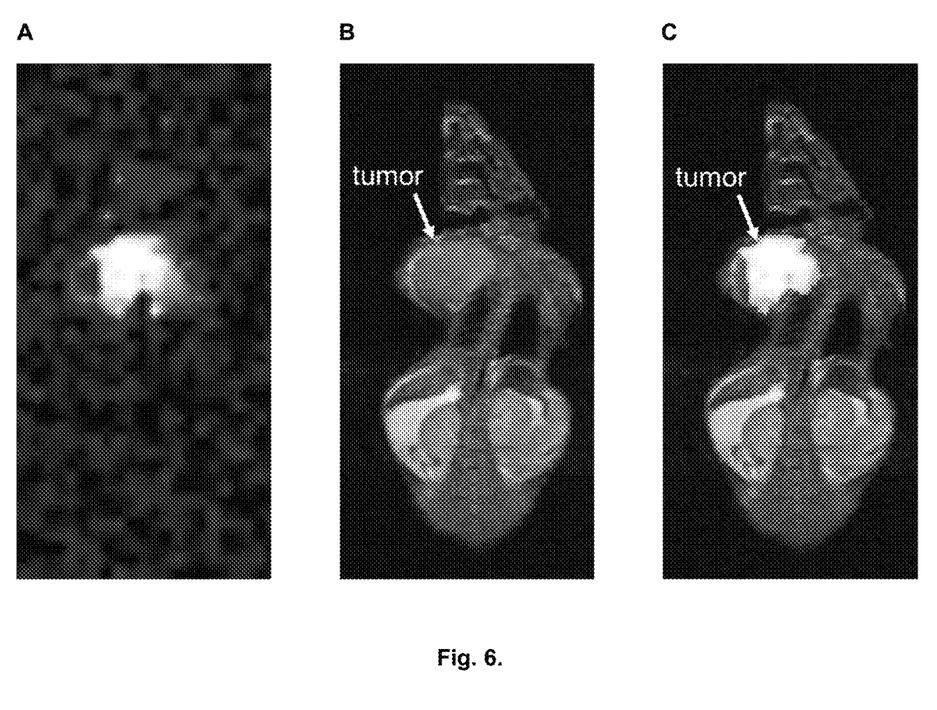
FIG. 6. MRI of a mouse with the breast carcinoma 4T1 40 min after the administration of 72 mg of 3-OCD$_3$-glucose:
  a) $^2$H MR image;
  b) $^1$H MR image;
  c) the combined MR image.

FIG. 6 shows the images obtained for the mouse no. 2 with tumor 40 minutes after intraperitoneal administration of 3-O-CD$_3$-glucose: (a) $^2$H MRI; b) $^1$H MRI; C) the superposition of $^2$H MRI and $^1$H MRI).

Figure 7:
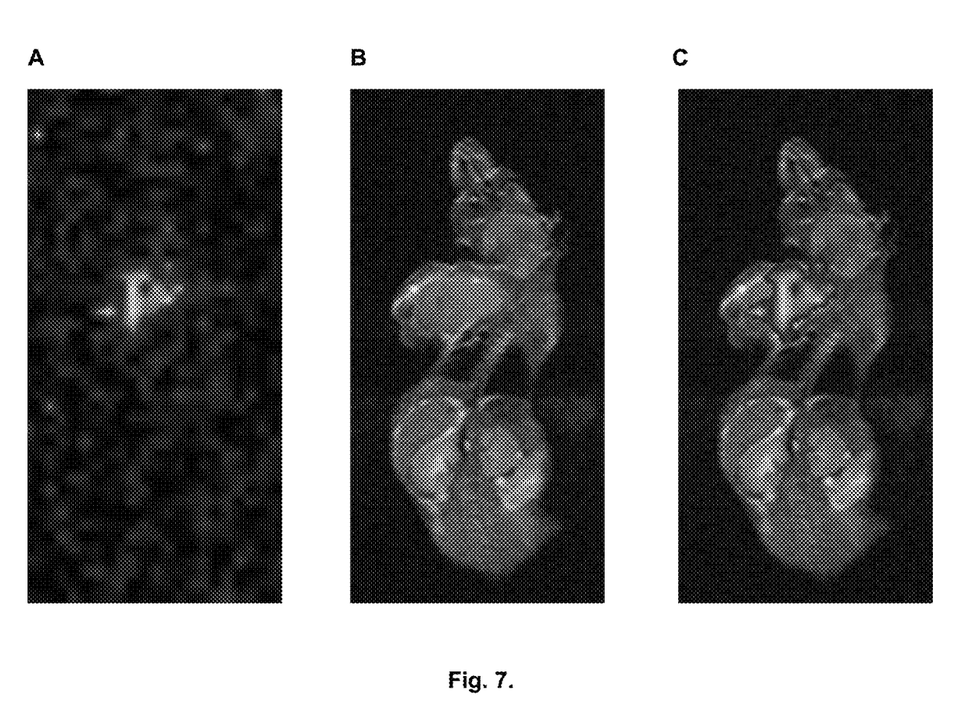
FIG. 7. MRI of a mouse with the breast carcinoma 4T1 210 min after the administration of 72 mg of 3-OCD$_3$-glucose:
  a) $^2$H MR image;
  b) $^1$H MR image;
  c) the combined MR image.

FIG. 7 shows the images obtained for the mouse no. 2 with the tumor 210 minutes after intraperitoneal administration of 3-O-CD$_3$-glucose: (a) $^2$H MRI; b) $^1$H MRI; C) the superposition of $^2$H MRI and $^1$H MRI).

Figure 8:
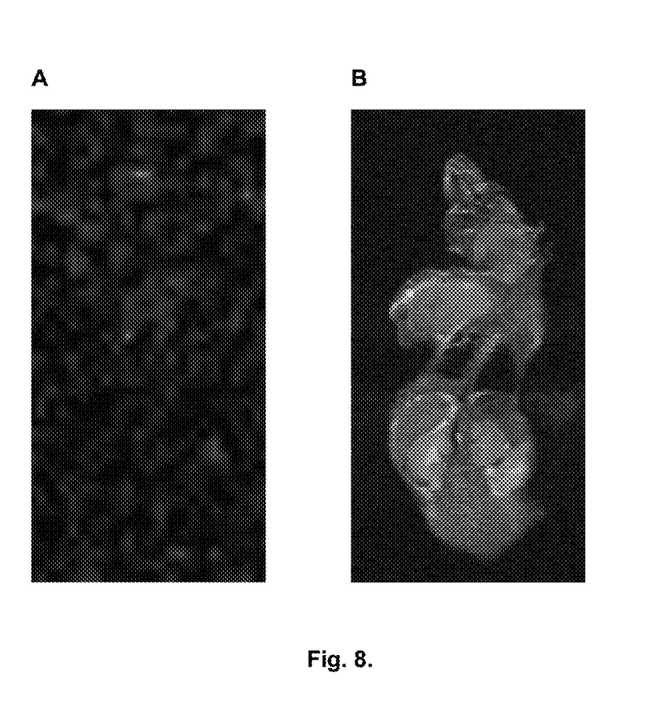
FIG. 8. MRI of a mouse with the breast carcinoma 4T1 320 min after the administration of 72 mg of 3-OCD$_3$-glucose:
 a) $^2$H MR image;
 b) $^1$H MR image.

FIG. 8 shows the images obtained for the mouse no. 2 with the tumor 320 min after intraperitoneal injection of 3-O-CD$_3$-glucose: (a) $^2$H MRI; b) $^1$H MRI.

FIGS. 5-8 demonstrate that the signal of the deuterium is predominantly localized in the region corresponding to the tumor according to $^1$H MRI.

Based on the results illustrated by FIGS. 5-8, we can conclude that:

1) the diagnostic agents according to the invention, in particular, 3-O-CD$_3$-glucose, is accumulated in the tumor in sufficient concentration to be visualized using $^2$H MRI;
2) the diagnostic agents according to the invention, in particular, 3-O-CD$_3$-glucose can be used for the detection of malignant tumors using $^2$H MRI.

Based on the results illustrated by FIGS. 5-8, we can conclude that the allowable time range between the introduction of the diagnostic agent according to the invention and detection of deuterium can reach, in particular for the mouse, 20-210 min. It should be noted that for other animals and for humans this range can be significantly wider due to the difference in pharmacokinetics. In addition, on the basis of these results we conclude that the diagnostic agent is removed from the tumor in several hours.

Figure 9:
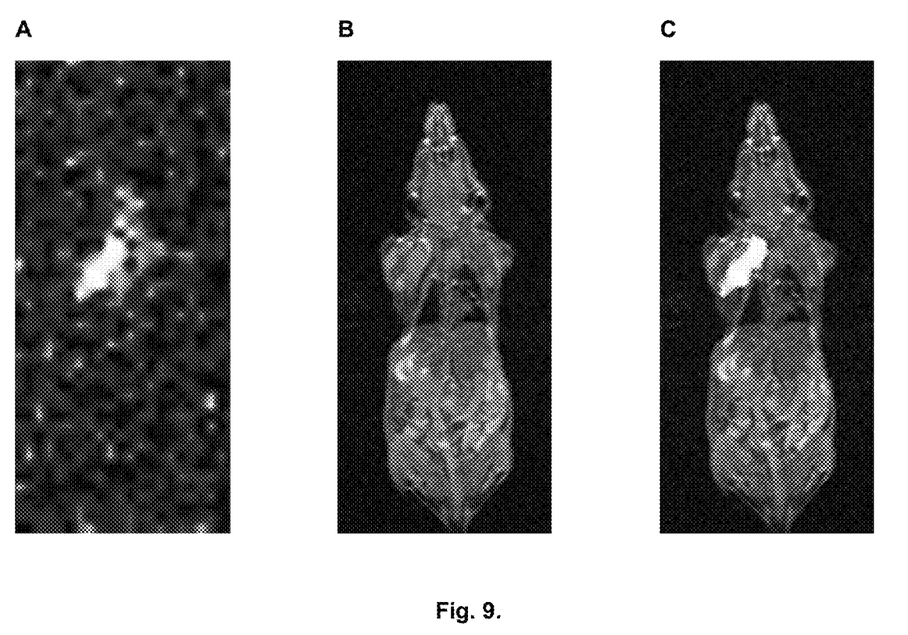
FIG. 9. MRI of the mouse with the breast carcinoma 4T1 50 min after the administration of 20 mg of 3-OCD$_3$-glucose:
 a) $^2$H MR image;
 b) $^1$H MR image;
 c) the combined MR image.

FIG. 9 shows the MR image obtained for the mouse no. 3 with tumor in 50 minutes after intravenous injection of 20 mg of 3-O-CD$_3$-glucose: (a) $^2$H MRI; (b) $^1$H MRI; (C) the superposition of $^2$H MRI and $^1$H MRI. This figure presents the accumulation of 3-O-CD$_3$-glucose in the tumor. The tumor volume measured using $^1$H MRI is 180 mm$^3$.

Based on the results illustrated by FIGS. 5-9, we can conclude that the valid range of the diagnostic agent doses can be at least 1-3.5 g of 3-O-CD$_3$-glucose per 1 kg of animal weight. It should be noted that for other animals and for humans, and in case of another route of administration (e.g. oral or intravenous) and/or other malignant diseases this range may be different. In particular, taking into account the allometric equations describing the pharmacokinetics of agents in organisms of different size, we can expect the reduction of a dose needed for human several-fold in comparison with the described doses.

Figure 10:
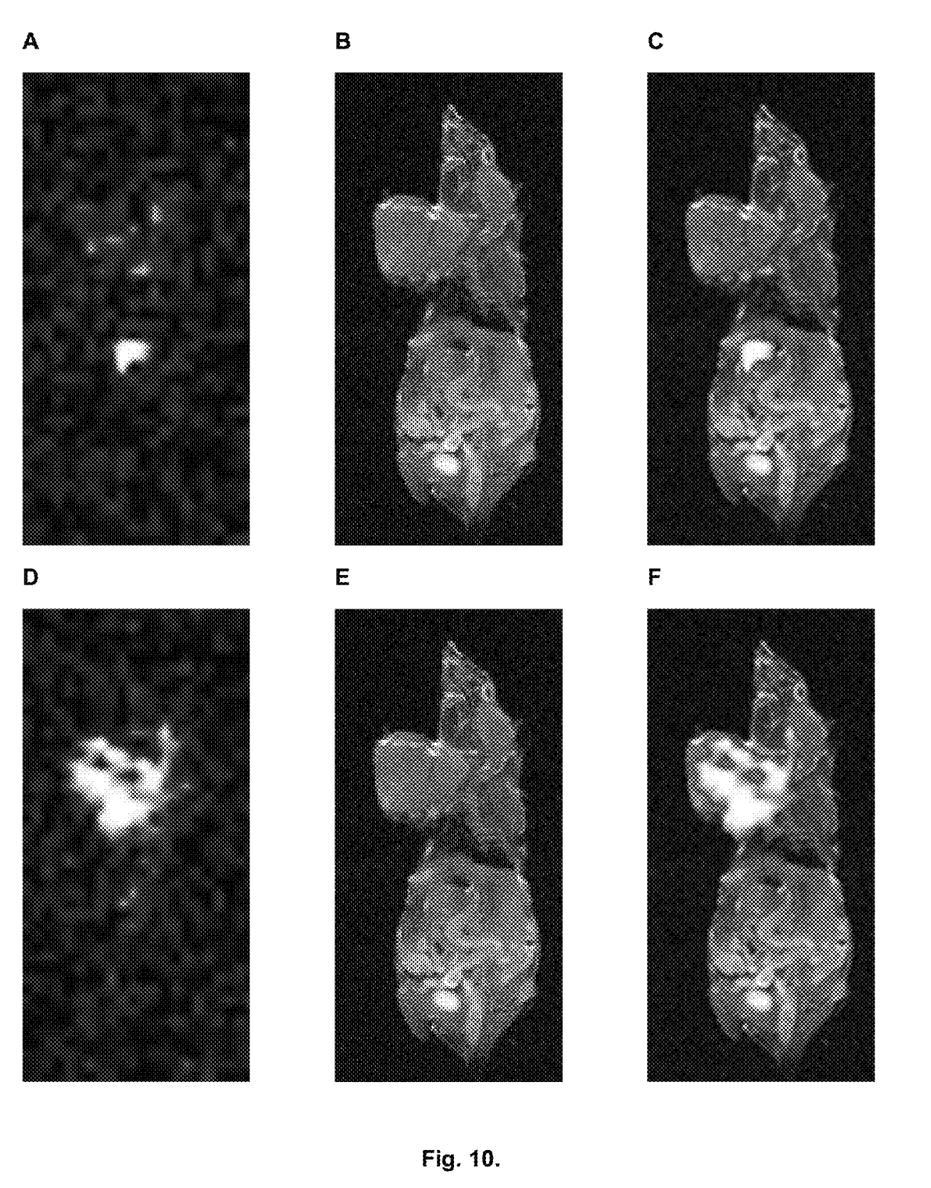
FIG. 10. MRI of a mouse with the breast carcinoma 4T1 after the oral administration of 70 mg of 3-OCD$_3$-glucose:
 (a) $^2$H MRI after 15 minutes;
 (b) $^1$H MRI after 15 minutes;
 (C) the superposition of $^2$H MRI and $^1$H MRI after 15 minutes;
 (g) $^2$H MRI after 100 minutes;
 (d) $^1$H MRI after 100 minutes;
 (e) the superposition of $^2$H MRI and $^1$H MRI after 100 minutes.

FIG. 10 shows the images obtained for the mouse no. 4, with tumor 15 and 100 min after oral administration of 70 mg of 3-O-CD$_3$-glucose: (a) $^2$H MRI after 15 minutes; (b) $^1$H MRI in 15 minutes; (C) the superposition of $^2$H MRI and $^1$H MRI after 15 minutes; (g) $^2$H MRI after 100 minutes; (d) $^1$H MRI after 100 minutes; (e) the superposition of $^2$H MRI and $^1$H MRI after 100 minutes. This figure shows how 3-O-CD$_3$-glucose, initially located in the stomach (15 min), over time, is accumulated in tumors (115 min).

Based on the results illustrated by FIG. 10, it can be concluded that the diagnostic agent according to the invention can be successfully used when administered orally.

Despite the fact that the invention has been described with reference to the disclosed embodiments, for specialists in this field it should be obvious that the specific details of the described experiments are given only for the purpose of illustrating the present invention and they should not be construed as in any way limiting the scope of the invention. It should be understood that it is possible to implement various modifications without deviation from the essence of the present invention.

The invention claimed is:

1. A method for diagnosing an oncological disease in a subject, the method comprising:
    a) administering to the subject a diagnostic agent comprising:
    a deuterated derivative of 3-O-methylglucose or a mixture of at least two different deuterated derivatives of 3-O-methylglucose,
    wherein the deuterated derivative of 3-O-methylglucose or the mixture of the at least two different deuterated derivatives of 3-O-methylglucose is formulated to accumulate in tumor cells in a concentration detectable in vivo by $^2$H magnetic resonance imaging, and/or magnetic resonance spectroscopy at a frequency of deuterium nuclei, in the diagnosis of the oncological disease, and
    wherein "deuterated" and "deuterated derivative" refer to a compound containing deuterium associated with carbon in excess of its natural content, at least in one position, and wherein "mixture of at least two different deuterated derivatives" refers to a mixture of compounds containing deuterium in different positions of the molecule, or containing different amounts of deuterium in the same position wherein the deuterated derivative of 3-O-methylglucose is a 3-O-CD3-glucose, 3-O-CD$_2$H-glucose, 3-O-CDH$_2$-glucose, 6,6-dideuterio-3-O-CD$_3$-glucose, 6,6-dideuterio-3-O-CD$_2$H-glucose, 6,6-dideuterio-3-O-CDH$_2$-glucose or 6,6-dideuterio-3-O—CH$_3$-glucose or at least two different deuterated derivatives of 3-O-methylglucose, selected from 3-O-CD$_3$-glucose and/or 3-O-CD$_2$H-glucose and/or 3-O-CDH$_2$-glucose and/or 6,6-dideuterio-3-O-CD$_3$-glucose and/or 6,6-dideuterio-3-O-CD$_2$H-glucose and/or 6,6-dideuterio-3-O-CDH$_2$-glucose and/or 6,6-dideuterio-3-O—CH$_3$-glucose and/or any other deuterated derivatives of 3-O-methyl glucose;
    b) conducting magnetic resonance imaging and/or magnetic resonance spectroscopy at the frequency of deuterium nuclei after administration of the diagnostic agent after a period of time sufficient for accumulation of said diagnostic agent in a tumor, for obtaining, respectively, a MR image and/or NMR spectrum; and
    c) diagnosing presence or absence of the oncological disease based on an observed signal intensity of deuterium nuclei, reflecting a level of accumulation of the diagnostic agent.

2. The method according to claim 1, wherein the subject is diagnosed with no cancer in case of absence of accumulation of the diagnostic agent.

3. The method according to claim 1, wherein at least one additional medical study, selected from magnetic resonance imaging at the frequency of nuclei differing from deuterium, or ultrasound, or computed tomography, or X-ray, or palpation, or biopsy, or screening of biological materials for tumor markers, or radionuclide diagnosis, or physical examination is carried out.

4. The method according to claim 1, wherein diagnosing the presence or absence of the oncological disease is based on comparison of the observed signal intensity of deuterium nuclei in the subject with a typical intensity of signal observed in healthy subjects in corresponding tissue or organ.

5. The method according to claim 3, wherein diagnosing the presence or absence of the oncological disease is based on comparison of the observed signal intensity of deuterium nuclei in regions corresponding to normal and pathological tissues according to the additional medical study.

6. The method according to claim 3, wherein diagnosing the presence or absence of the oncological disease is based on a comparison of the observed signal intensity of deuterium nuclei in neighboring voxels that are located at different sides of an interface between normal tissue and tissue suspicious for a tumor according to $^1$H MRI.

7. The method according to the claim 3, wherein diagnosing the presence or absence of the oncological disease is based on a comparison of deuterium images with $^1$H magnetic resonance images from the same subject.

8. The method according to claim 1, wherein the observed signal intensity of deuterium nuclei and/or its change in time enables a conclusion on structure, malignancy grade, aggressiveness, or degree of differentiation of a tumor to be made.

9. The method according to claim 1, wherein the oncological disease is breast cancer.

10. The method according to claim 1, wherein during MR image registration, a selective excitation of deuterium nuclei of the diagnostic agent is used.

11. The method according to claim 1, wherein the diagnostic agent is administered to the subject orally.

12. The method according to claim 1, wherein the magnetic resonance tomography and/or magnetic resonance spectroscopy is carried out 20-210 minutes after administration of the diagnostic agent.

13. The method according to claim 1, wherein the diagnostic agent is administered to the subject in an amount corresponding to 1-3.5 g deuterated 3-O-methylglucose or mixture of deuterated derivatives of 3-O-methylglucose per 1 kg of body weight of the subject.

14. The method according to claim 1, wherein the diagnostic agent comprises at least one of 3-O-$CD_3$-glucose, 3-O-$CD_2$H-glucose, 3-O-$CDH_2$-glucose, 6,6-dideuterio-3-O-$CD_3$-glucose, 6,6-dideuterio-3-O-$CD_2$H-glucose, 6,6-dideuterio-3-O-$CDH_2$-glucose, and 6,6-dideuterio-3-O—$CH_3$-glucose.

15. The method according to claim 1, wherein the diagnostic agent comprises a mixture of at least two different deuterated derivatives of 3-O-methylglucose.

* * * * *